United States Patent
Ory et al.

(10) Patent No.: US 6,575,897 B1
(45) Date of Patent: Jun. 10, 2003

(54) SUSPENSION DEVICE FOR TREATING PROLAPSE AND URINARY INCONTINENCE

(75) Inventors: Francois Regis Ory, Fontaines Saint Martin (FR); Michel Therin, Lyons (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 09/830,717

(22) PCT Filed: Nov. 9, 1999

(86) PCT No.: PCT/FR99/02751

§ 371 (c)(1),
(2), (4) Date: May 21, 2001

(87) PCT Pub. No.: WO00/27304

PCT Pub. Date: May 18, 2000

(30) Foreign Application Priority Data

Nov. 10, 1998 (FR) .............................. 98 14306

(51) Int. Cl.[7] .................................. A61F 2/02
(52) U.S. Cl. ....................................... 600/30
(58) Field of Search .............................. 600/30, 29, 37; 128/897, 898, 885–887, DIG. 25; 606/65, 232, 67, 72, 73, 75, 151; 623/12.16

(56) References Cited

U.S. PATENT DOCUMENTS

| 5,013,292 A | | 5/1991 | Lemay |
| 5,474,543 A | | 12/1995 | McKay |
| 5,647,836 A | | 7/1997 | Blake, III et al. |
| 6,039,686 A | * | 3/2000 | Kovac .......................... 600/30 |
| 6,042,534 A | * | 3/2000 | Gellman et al. .............. 600/30 |

FOREIGN PATENT DOCUMENTS

| DE | 195 44 162 C1 | 4/1997 |
| EP | 0 643 945 A2 | 3/1995 |
| WO | WO 90/12551 | 11/1990 |

* cited by examiner

Primary Examiner—Max F. Hindenburg
Assistant Examiner—Brian Szmal
(74) Attorney, Agent, or Firm—Oliff & Berridge, PLC

(57) ABSTRACT

The device comprises at least one filiform suspension cord, made of nonabsorbable material and with limited elasticity, and at least two anchoring parts connected to the ends of this cord; these anchoring parts are made of sheet material, having a flexible and openworked structure, capable of adapting to the configuration of the respective implantation walls, and said parts are intended to be fixed to these same walls by appropriate means, such as suturing or stapling, and then to be incorporated in these walls by regrowth of tissue through them.

14 Claims, 4 Drawing Sheets

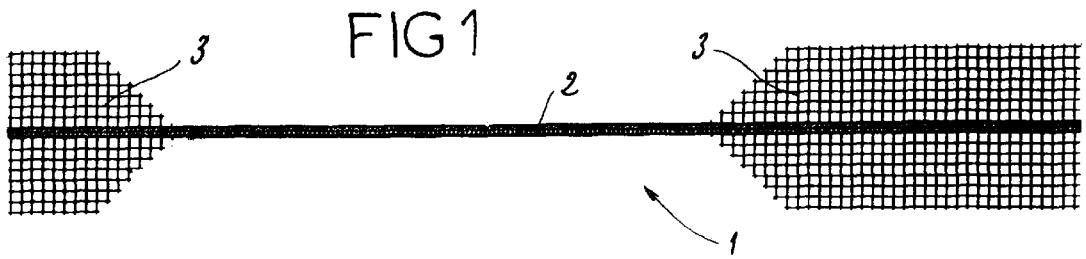
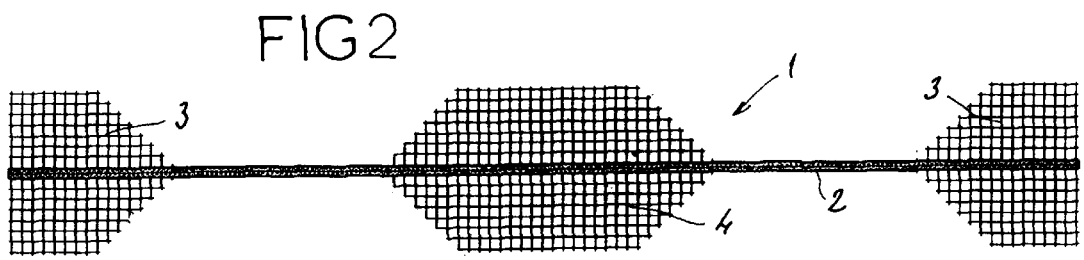
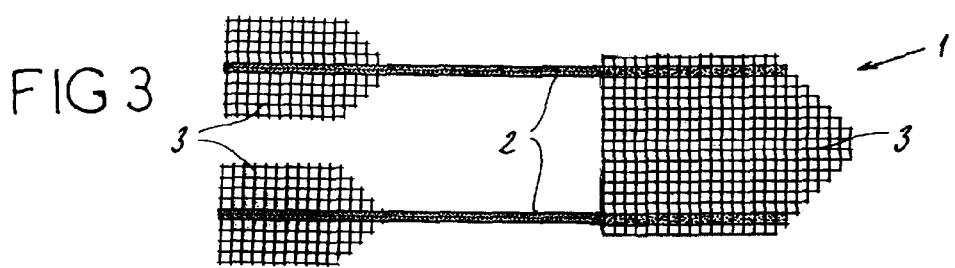
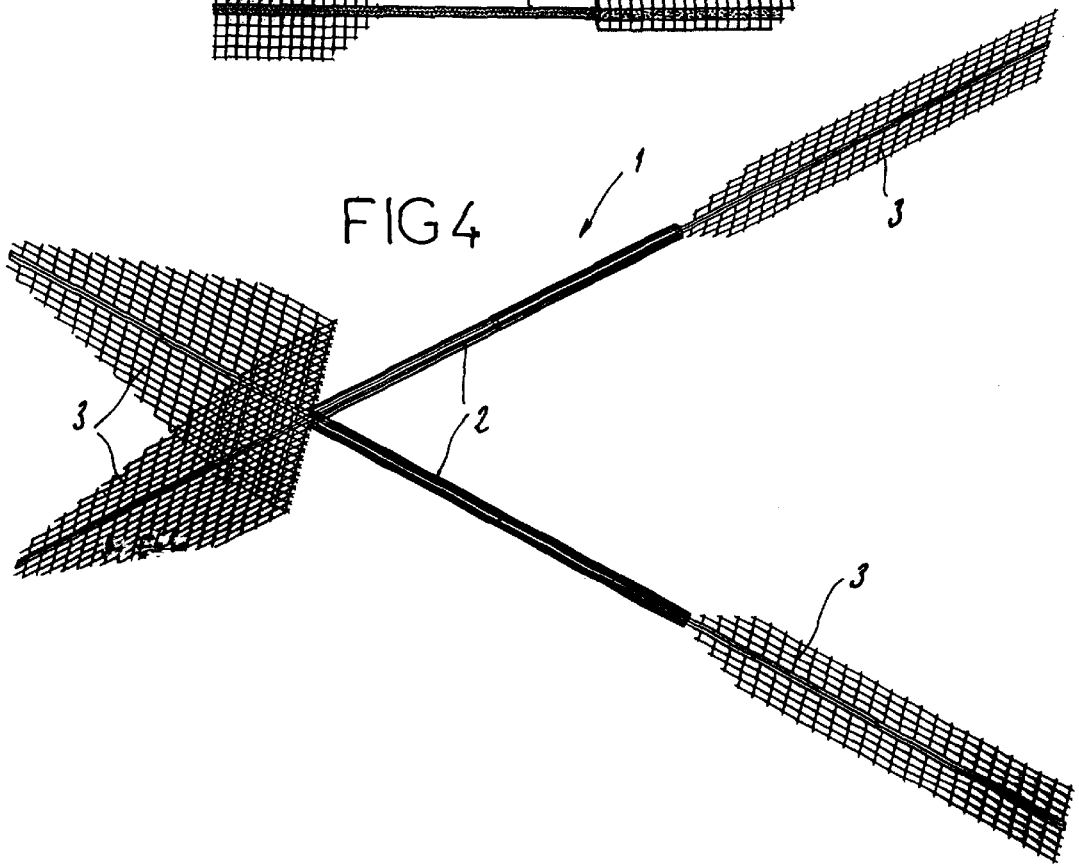

SUSPENSION DEVICE FOR TREATING PROLAPSE AND URINARY INCONTINENCE

The present invention relates to a suspension device for surgically treating prolapse, in particular genital, urinary and rectal prolapse, and urinary incontinence in elderly women.

Genital, urinary and rectal prolapses result from a slackening of the tissues supporting the organs, and of the perineum. Their surgical treatment involves connecting one or more of these organs (bladder, vagina, uterus, rectum) to anatomically stable zones, in particular, anteriorly, at Cooper's ligament, on the postero-superior margin of the pubis or, posteriorly, at the area of the promontory, that is to say the antero-superior angle of the sacrum, by "suspending" these organs on these anatomically stable zones.

Surgical treatment of prolapses is presently carried out using nonabsorbable sutures or strips for strengthening of walls.

Sutures have the advantage of being easy to put in place during treatment of a prolapse by open surgery, of having a low cost and of having extensive possibilities of use.

However, they have the disadvantage of providing a punctiform and somewhat inelastic fixation of the suspension filament, which is likely to cause shearing of the tissues on which they are placed, leading to rupturing of the anchoring arrangement. The result of this is that their efficacy is limited in time. Moreover, they are complicated to put into place when treating prolapses by laparoscopy, given the need to form numerous knots.

Strips have the advantage of being easy to put into place irrespective of the route employed (open surgery or laparoscopy), of being effective, and of allowing the stresses which are exerted to be distributed at a plurality of anchoring points. They are also capable of rapid incorporation in the anchoring wall by means of tissue growth.

However, these strips have the disadvantage of having to be twisted when the respective implantation walls are not parallel. The twisted zone acts in scarcely favorable conditions, moving along the band when tension is applied, with the latter becoming thinner at its center, making it difficult to put into place and accentuating the shearing effect. A band of relatively rigid material, such as monofilament polypropylene, has edges which could damage the surrounding tissues along the entire length of the band.

There is at present no available implant which is entirely satisfactory for specific treatment of prolapse and urinary incontinence, and the present invention aims to remedy this deficit.

To this end, the device to which the invention relates comprises at least one filiform suspension cord, made of nonabsorbable material and with limited elasticity, and at least two anchoring parts connected to the ends of this cord; these anchoring parts are made of sheet material, having a flexible and openworked structure, capable of adapting to the configuration of the respective implantation walls, and said parts are intended to be fixed to these same walls by appropriate means, such as suturing or stapling, and then to be incorporated in these walls by regrowth of tissue through them.

Thus, unlike the means employed in the prior art, the device according to the invention has a dual structure, each component (cord or anchoring parts) being optimized for the function which it is intended to fulfill: the cord, because it is filiform, does not damage the surrounding tissues, and any twisting thereof is without any consequence on its pulling action and hence on its strength over the course of time, or on the maneuverability of the device; by virtue of the elasticity of this cord, the surgeon can adapt the tension of the suspension without disturbing the anchoring zones; the anchoring parts can be adapted to the shape of their anchoring site and can be fixed thereto at a plurality of mutually remote points and then be incorporated in the walls on which they are anchored by regrowth of tissue through them.

The ruptures of the sutures as a result of shearing at the anchoring points are eliminated and the openworked structure of the anchoring parts permits early and intimate tissue incorporation, without formation of a peripheral fibrous shell, for the purpose of a functional recovery and a rapid convalescence of the patient.

According to one embodiment of the invention, the device comprises a cord and two anchoring parts, one of which is fixed to one of the ends of the cord, and the other of which is fixed to the other of these ends.

One of the anchoring parts is intended to be fixed to the organ to be suspended, and the other to the anatomically stable zone. This device can be used in particular, singly or doubly, to permit a posterior uterine or rectal suspension with anchoring in the area of the promontory, or a cystopexy by suspension of the anterior and lateral walls of the vagina on Cooper's ligament (called the Burch technique).

According to another embodiment of the invention, the device comprises a cord, two anchoring parts fixed to each of the ends of the cord, and an anchoring part fixed at a defined site along the length of the cord, in particular in the median zone thereof.

The anchoring parts fixed to the ends of the cord are connected to the anatomically stable zone, while the anchoring part fixed at a defined site along the length of the cord surrounds part of the organ to be suspended, in the manner of a sling. The device configured in this way can be used in particular for cystopexy with a subcervical sling.

According to yet another embodiment of the invention, the device comprises two cords which are each equipped with an anchoring part connected to one of their ends, the two other ends of these cords being connected to a single anchoring part.

The anchoring parts connected to one of the ends of the cords are intended to be fixed to the anatomically stable zone, while said single anchoring part is intended to be fixed to the organ to be suspended. This device can be used in particular to permit vaginal suspension on the promontory in cases where the uterus is not removed.

The cords can be parallel or form an angle with each other.

According to yet another embodiment of the invention, the device comprises two cords which are each equipped with an anchoring part connected to one of their ends, the two other ends of the cords being connected to two anchoring parts, which are themselves connected to one another in the area of one of their edges.

These two anchoring parts when assembled thus have a leaf shape allowing the whole arrangement to be engaged either side of part of an organ, in particular on the end of this organ, which it can "cap". The device configured in this way can be used in particular for suspension of the vagina on the promontory after hysterectomy.

The cord is preferably made of a braid of yarns of polypropylene or polyethylene terephthalate (polyester).

The elasticity curve of this cord is as linear as possible so as to allow the operating surgeon to adjust the tension. A tensile strength of ten kilos is easily sufficient, and an elongation at break of the order of 40% obtained linearly from a load of one or two kilos is preferable.

The cord is preferably made of a warp-knitted braid formed by four two-ended yarns of textured 167 decitex polyester.

This cord advantageously has a cross section greater than about one square millimeter in order to avoid any cutting action on the surrounding tissues during tensioning.

The anchoring parts can be made of a knitted or non-woven lattice, preferably of polypropylene or polyethylene terphthalate (polyester), of the type used for strengthening walls after treatment of inguinal hernias. They have shapes and dimensions adapted to the anchoring to be performed and they are preferably of a very openworked structure to permit the aforementioned regrowth of tissue through them.

The material of the cord and of the anchoring parts is preferably identical.

The cord and the anchoring parts can be joined by stitching or welding, in particular by ultrasound.

To ensure that it is fully understood, the invention is again described below with reference to the attached diagrammatic drawing which shows, by way of nonlimiting examples, several embodiments of the suspension device to which the invention relates.

FIGS. 1 to 3 are flat views of three embodiments thereof;

FIG. 4 is a perspective view of a fourth embodiment;

For simplification, elements which are found in these different embodiments or which are similar from one embodiment to another have been labeled with the same reference numbers.

FIG. 1 shows a suspension device 1 for surgically treating prolapse, in particular genital, urinary or rectal prolapse in elderly women.

This device comprises a cord 2 and two anchoring parts 3 fixed to the ends of the cord 1.

The cord 2 is filiform and is made of a warp-knitted braid formed by four two-ended yarns of textured 167 decitex polyester.

The anchoring parts 3 are made of a knitted lattice of polyester yarns identical to those forming the cord 2. They have a flexible and openworked structure which is capable of adapting to the configuration of the walls of the anchoring zones or organs to be suspended, and they have shapes and dimensions adapted to the anchoring which is to be performed.

These anchoring parts 3 are fixed to the cord 2 by stitching or welding, in particular by ultrasound.

Figure 5:
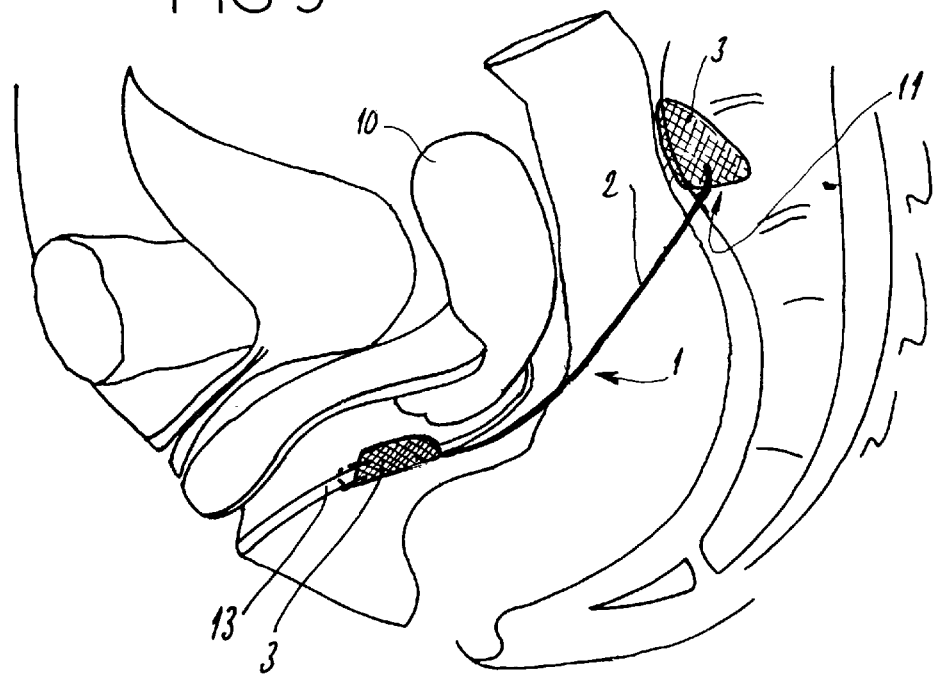
FIG. 5 is a very simplified sectional view of the lower trunk of an individual, where a device of the type shown in FIG. 1 has been used to perform a posterior suspension of the vagina, with anchoring on the promontory.

FIG. 5 shows a posterior suspension of the vagina 13 on the promontory 11, performed using a device 1 of this type, the anchoring parts 3 being fixed to the respective implantation walls by suturing or stapling, and subsequently being incorporated in these walls by regrowth of tissue through them.

Figure 6:
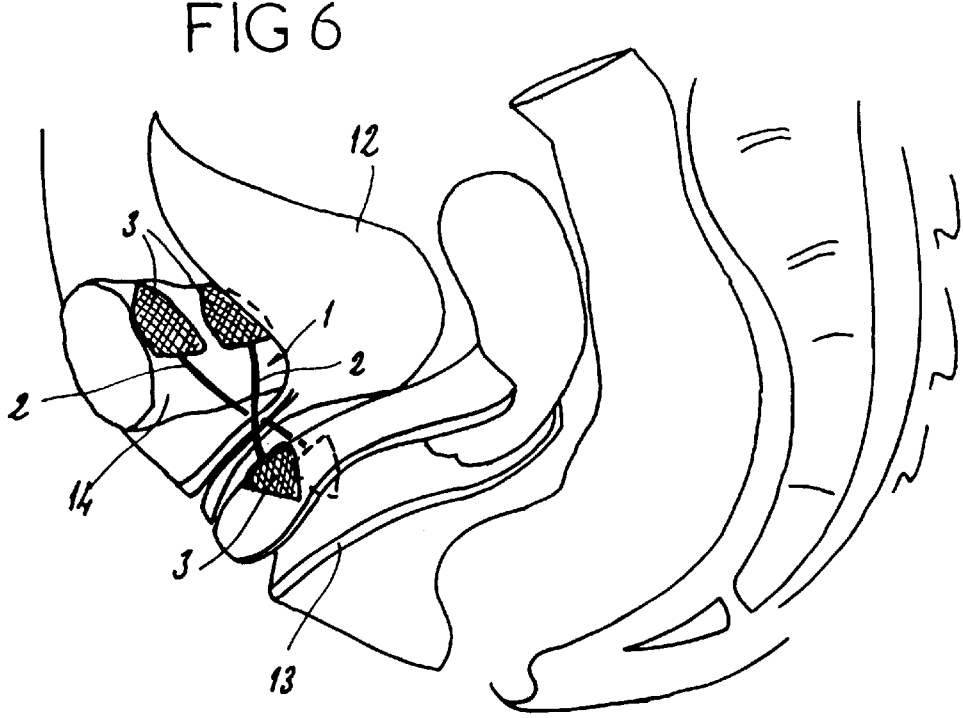
FIG. 6 is a view similar to FIG. 5, where two devices of the type shown in FIG. 1 have been used to perform a cystopexy with suspension of the anterior and lateral walls of the vagina on Cooper's ligament.

FIG. 6 shows a cystopexy, that is to say support of the bladder 12 by suspension of the anterior and lateral walls of the vagina 13 on Cooper's ligament 14, using the Burch technique, and using two devices 1 of the type shown in FIG. 1.

Figure 7:
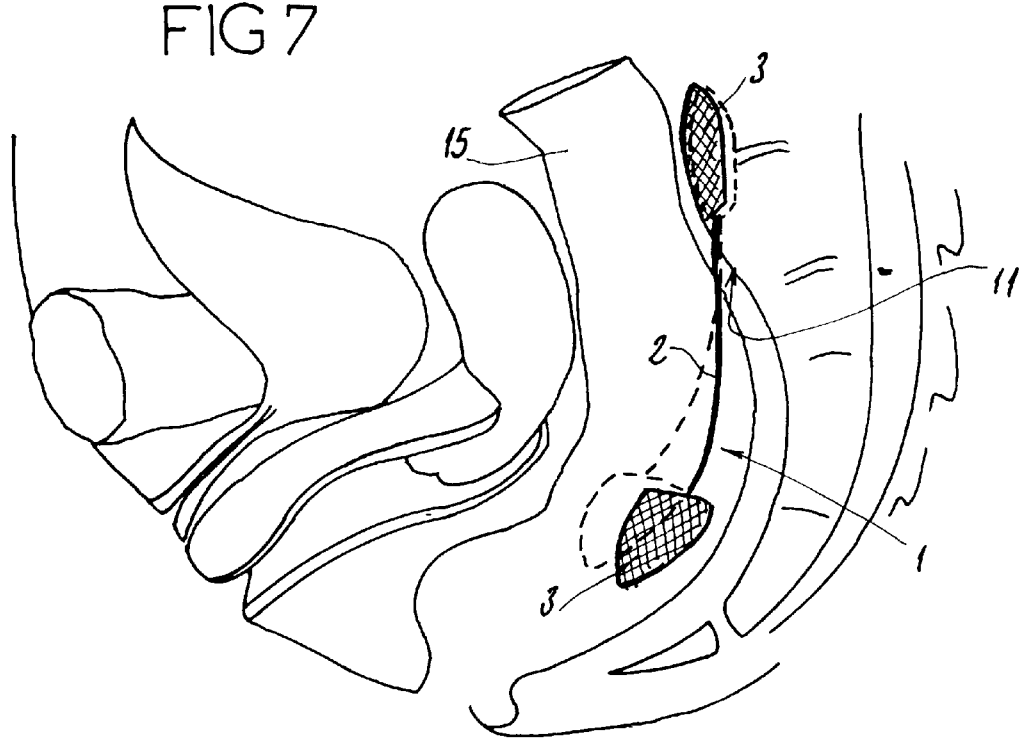
FIG. 7 is a view similar to FIG. 5, where two devices of the type shown in FIG. 1 have been used to perform a posterior suspension of the rectum, with anchoring on the promontory.

FIG. 7 in turn shows a posterior suspension of the rectum 15, with anchoring on the promontory 11, performed using two devices of the type shown in FIG. 1, the anchoring parts 3 fixed to the promontory 11 being superposed while the two other anchoring parts 3 are fixed either side of the rectum 15.

FIG. 2 shows a device 1 comprising a cord 2 and two anchoring parts 3 of the type mentioned above which are fixed to each of the ends of the cord 2. This device 1 additionally comprises an anchoring part 4 similar to the anchoring parts 3 and fixed in the median zone of the cord 2.

Figure 8:
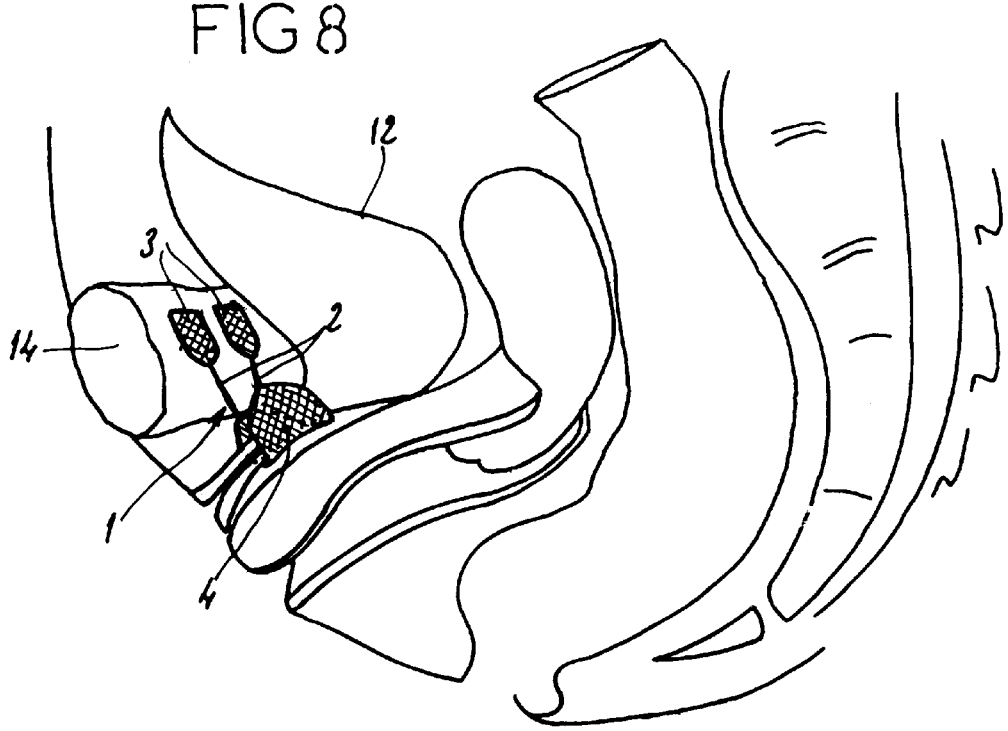
FIG. 8 is a view similar to FIG. 5, where a device shown in FIG. 2 has been used to perform a cystopexy using a subcervical sling.

As can be seen in FIG. 8, in the case of a cystopexy using a subcervical sling, the anchoring parts 3 are fixed to Cooper's ligament 14 while the anchoring part 4 surrounds the neck of the bladder in the manner of a sling.

FIG. 3 shows another device 1 comprising two parallel cords 2 which are each equipped with an anchoring part 3 connected to one of their ends, the two other ends of the cords 2 being connected to a single anchoring part 3 whose dimensions are greater than those of the other two parts 3.

Figure 9:
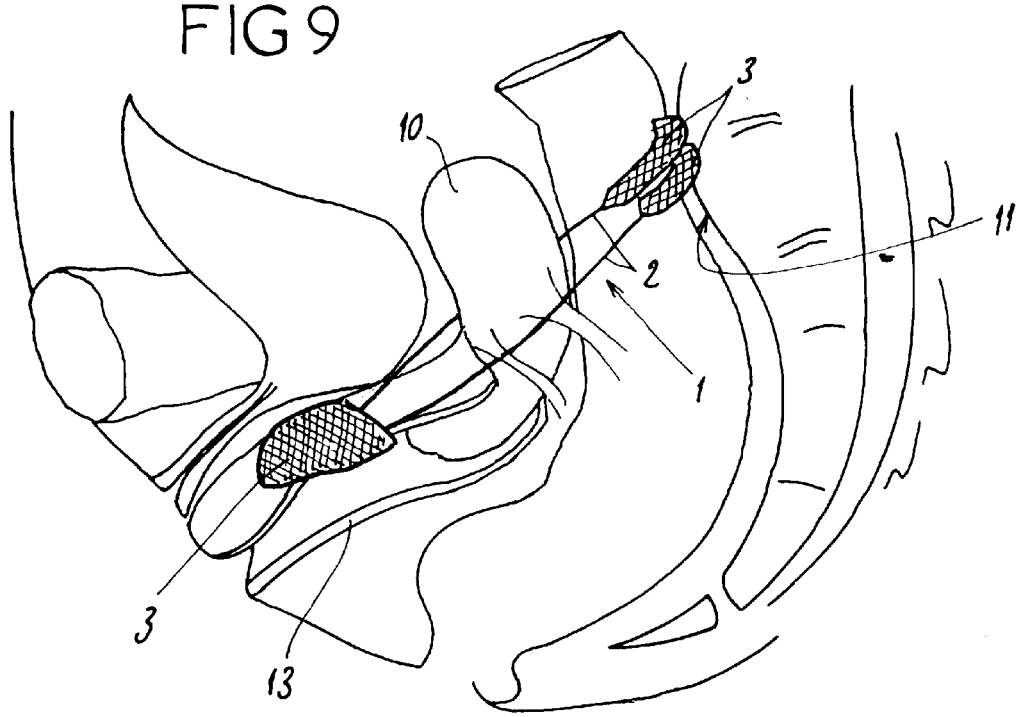
FIG. 9 is a view similar to FIG. 5, where a device of the type shown in FIG. 3 has been used to perform a suspension of the vagina with anchoring on the promontory, the uterus not being removed.

As is shown in FIG. 9, in the case of a suspension of the vagina 13 on the promontory 11, and where the uterus 10 is retained, the anchoring parts 3 connected to the two ends of the cords 2 are fixed to the promontory 11 while the single anchoring part 3 is fixed to the anterior face of the vagina 13, the two cords 2 passing either side of the uterus 10.

FIG. 4 shows still another device 1 comprising two cords 2 which are equipped with anchoring parts 3 connected to their ends. Two anchoring parts 3 are connected to one another at one of their edges.

Figure 10:
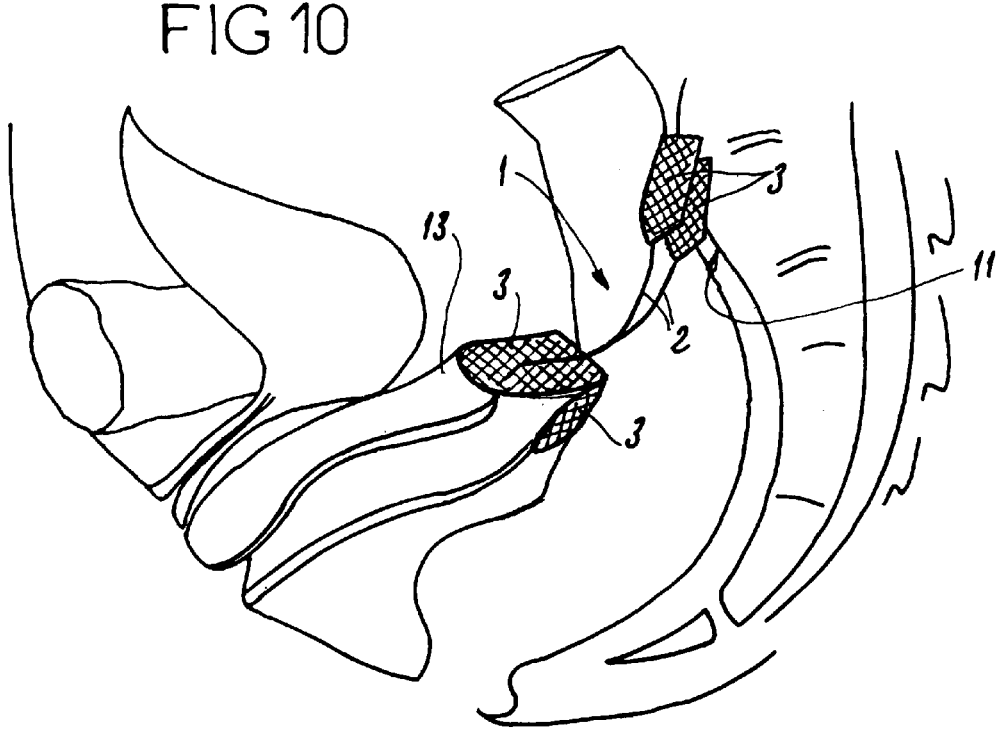
FIG. 10 is a view similar to FIG. 5, where a device of the type shown in FIG. 4 has been used to perform a vaginal suspension with anchoring on the promontory, after hysterectomy.

These two anchoring parts 3 thus have a leaf shape which, as shown in FIG. 10 in the case of a suspension of the vagina 13 on the promontory 11 after hysterectomy, allows them to cap the end of the vagina 13.

The invention thus makes available a suspension device for surgically treating prolapse, in particular genital, urinary and rectal prolapse, and urinary incontinence in elderly women, and which remedies the disadvantages of the similar devices of the prior art. This is because, unlike the means employed in the prior art, this device has a dual structure, each component (cord or anchoring parts) being optimized for the function which it is intended to fulfill: the cord, because it is filiform, does not damage the surrounding tissues, and any twisting thereof is without any consequence on its pulling action and hence on its strength over the course of time, or on the maneuverability of the device; by virtue of the elasticity of this cord, the surgeon can adapt the tension of the suspension without disturbing the anchoring zones; the anchoring parts can be adapted to the shape of their anchoring site and can be fixed thereto at a plurality of mutually remote points and then be incorporated in the walls on which they are anchored by regrowth of tissue through them.

It goes without saying that the invention is not limited to the embodiment described above by way of example and that instead it encompasses all variants thereof. Thus, it will be evident that the dimensions and shapes of the anchoring parts 3 can differ slightly from one application to another so as to have a shape adapted to the configuration of the corresponding implantation wall.

Likewise, it will be appreciated that the drawing is purely diagrammatic and illustrative. In particular, the anatomical zones for implantation of the anchoring parts 3 can vary as a function of developments in surgical techniques. Those shown in FIGS. 5 through 10 constitute only an aid to understanding the suspension device according to the invention and they are not intended to be representative of the real anatomy of this region.

What is claimed is:

1. A suspension device for surgically treating prolapse and urinary incontinence in an elderly woman, comprising:
   at least one filiform suspension cord, made of nonabsorbable material and with limited elasticity, and
   at least two anchoring parts connected to ends of the at least one cord;
   wherein said anchoring parts are made of sheet material, having a flexible and openworked structure, capable of adapting to the configuration of implantation walls, and
   wherein said anchoring parts are intended to be fixed to said walls and then to be incorporated in said walls by regrowth of tissue through said anchoring parts.

2. The suspension device as claimed in claim 1, comprising a filiform suspension cord and first and second anchoring parts; wherein said first anchoring part is fixed to a first end of the cord, and said second anchoring part is fixed to a second end of the cord.

3. The suspension device as claimed in claim 1, comprising:
   a filiform suspension cord having a length, and
   first, second and third anchoring parts;
   wherein said first anchoring part is fixed to a first end of the cord, and said second anchoring part is fixed to a second end of the cord, and
   wherein said third anchoring part is fixed at a defined site along the length of the cord.

4. The suspension device as claimed in claim 1, comprising:
   first and second filiform suspension cords each having first and second ends, and
   first, second and third anchoring parts;
   wherein said first end of said first cord is equipped with said first anchoring part, said second end of said second cord is equipped with said second anchoring part, and
   wherein said second end of said first cord and said first end of said second cord are both connected to said third anchoring part.

5. The suspension device as claimed in claim 1, comprising:
   first and second filiform suspension cords each having first and second ends, and
   first, second, third and fourth anchoring parts each having edges;
   wherein said first end of said first cord is equipped with said first anchoring part and said second end of said first cord is equipped with said second anchoring part,
   wherein said first end of said second cord is equipped with said third anchoring part and said second end of said second cord is equipped with said fourth anchoring part, and
   wherein said second and said third anchoring part are connected to one another in an area of one of their edges.

6. The suspension device as claimed in claim 1, wherein the at least one filiform suspension cord is made of a knitted braid of yarns selected from the group consisting of polypropylene and polyethylene terephthalate.

7. The suspension device as claimed in claim 6, wherein the at least one filiform suspension cord is made of a warp-knitted braid formed by four double yarns of textured 167 decitex polyester.

8. The suspension device as claimed in claim 1, wherein the at least one filiform suspension cord has a cross section greater than one square millimeter.

9. The suspension device as claimed in claim 1, wherein the at least two anchoring parts are made of a knitted or nonwoven lattice.

10. The suspension device as claimed in claim 1, wherein the at least one filiform suspension cord and the at least two anchoring parts are joined by a method selected from the group consisting of stitching, welding and ultrasound.

11. The suspension device as claimed in claim 3, wherein said third anchoring part is fixed at a median zone of the cord.

12. The suspension device as claimed in claim 9, wherein the at least two anchoring parts (3) are made of a knitted or nonwoven lattice selected from the group consisting of polypropylene and polyethylene terephthalate.

13. The suspension device as claimed in claim 9, wherein the at least two anchoring parts are made of a knitted or nonwoven lattice of the type used for strengthening walls after treatment of inguinal hernias.

14. A method of surgically treating prolapse and urinary incontinence in an elderly woman, comprising implanting at least one device according to claim 1 into the woman.

* * * * *